(12) United States Patent
Jakobsen

(10) Patent No.: US 12,337,156 B2
(45) Date of Patent: Jun. 24, 2025

(54) PISTON ROD DRIVE MECHANISM

(71) Applicant: Novo Nordisk A/S, Bagsvaerd (DK)

(72) Inventor: Nikolaj Eusebius Jakobsen, Soeborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 658 days.

(21) Appl. No.: 17/777,216

(22) PCT Filed: Dec. 3, 2020

(86) PCT No.: PCT/EP2020/084481
§ 371 (c)(1),
(2) Date: May 16, 2022

(87) PCT Pub. No.: WO2021/110842
PCT Pub. Date: Jun. 10, 2021

(65) Prior Publication Data
US 2022/0387725 A1    Dec. 8, 2022

(30) Foreign Application Priority Data
Dec. 4, 2019 (EP) ..................................... 19213596

(51) Int. Cl.
*A61M 5/315* (2006.01)
(52) U.S. Cl.
CPC .... *A61M 5/31583* (2013.01); *A61M 5/31541* (2013.01); *A61M 5/31551* (2013.01); *A61M 2005/3154* (2013.01)
(58) Field of Classification Search
CPC .......... A61M 5/31583; A61M 5/31541; A61M 5/31551
See application file for complete search history.

(56) References Cited

U.S. PATENT DOCUMENTS

| 8,226,631 B2 * | 7/2012 | Boyd ................ A61M 5/31555 604/209 |
| 2007/0123829 A1 * | 5/2007 | Atterbury ......... A61M 5/31535 604/207 |

(Continued)

FOREIGN PATENT DOCUMENTS

| EP | 3348298 A1 | 7/2018 |
| JP | 2014513587 A | 6/2014 |

(Continued)

*Primary Examiner* — Dung T Ulsh
(74) *Attorney, Agent, or Firm* — Wesley Nicolas

(57) ABSTRACT

The present invention provides a piston rod displacement mechanism for a pen injection device, comprising: a tubular housing (2) extending along a reference axis and comprising an interior housing surface (3) with a first engagement structure (4), a nut member (5) fixed within the tubular housing (2), a piston rod (15) comprising a first non-self-locking thread (18) having a first thread direction and a first thread pitch and being engaged with the nut member (5), and a second non-self-locking thread (17) superposed on the first non-self-locking thread (18), the second non-self-locking thread (17) having a second thread direction and a second thread pitch, and a dose dial sleeve (20) operable to advance the piston rod (15) in the nut member (5), the dose dial sleeve (20) comprising an exterior sleeve surface (21) with a second engagement structure (24) being in sliding engagement with the first engagement structure (4), and an interior sleeve surface (23) with a third engagement structure (29) being engaged with the second non-self-locking thread (17). One of the first engagement structure (4) and the second engagement structure (24) comprises a closed-circuit track configuration and the other of the first engagement structure and the second engagement structure comprises a track follower, and the closed-circuit track configuration comprises a helical track portion (24*h*) having a helical track direction equaling the second thread direction and a helical (Continued)

track pitch equaling the second thread pitch, and an axial track portion (24*a*) extending between a distal track end (24*d*) and a proximal track end (24*p*) and being connected to the helical track portion (24*h*) at the distal track end (24*d*).

10 Claims, 2 Drawing Sheets

(56) References Cited

U.S. PATENT DOCUMENTS

2014/0142511 A1* 5/2014 Gilmore .................. G01D 5/25
                                                                      604/189
2019/0009036 A1    1/2019 Bostrom

FOREIGN PATENT DOCUMENTS

| WO | 2009080775 A1 | 7/2009 |
| WO | 2009092807 A1 | 7/2009 |
| WO | 2011039233 A1 | 4/2011 |
| WO | 2012125133 A1 | 9/2012 |
| WO | 2013010884 A1 | 1/2013 |
| WO | 2018185317 A1 | 10/2018 |
| WO | 19166469 | 9/2019 |

* cited by examiner

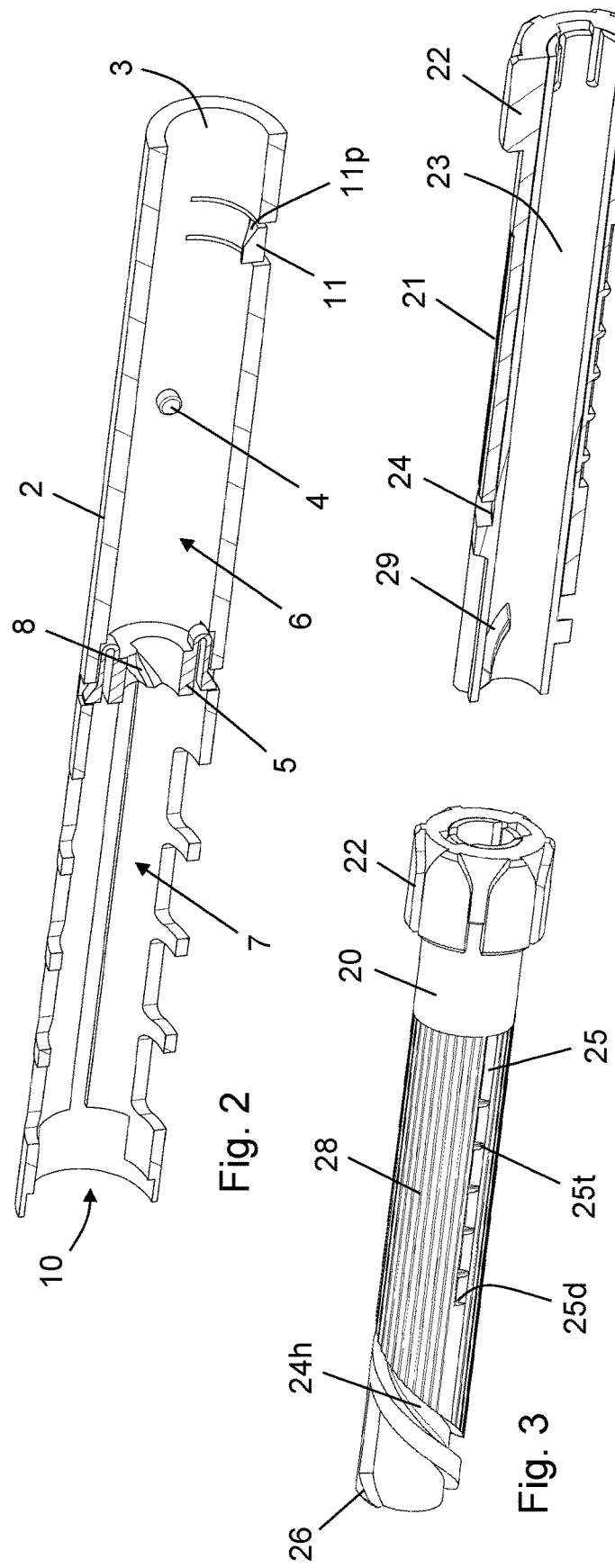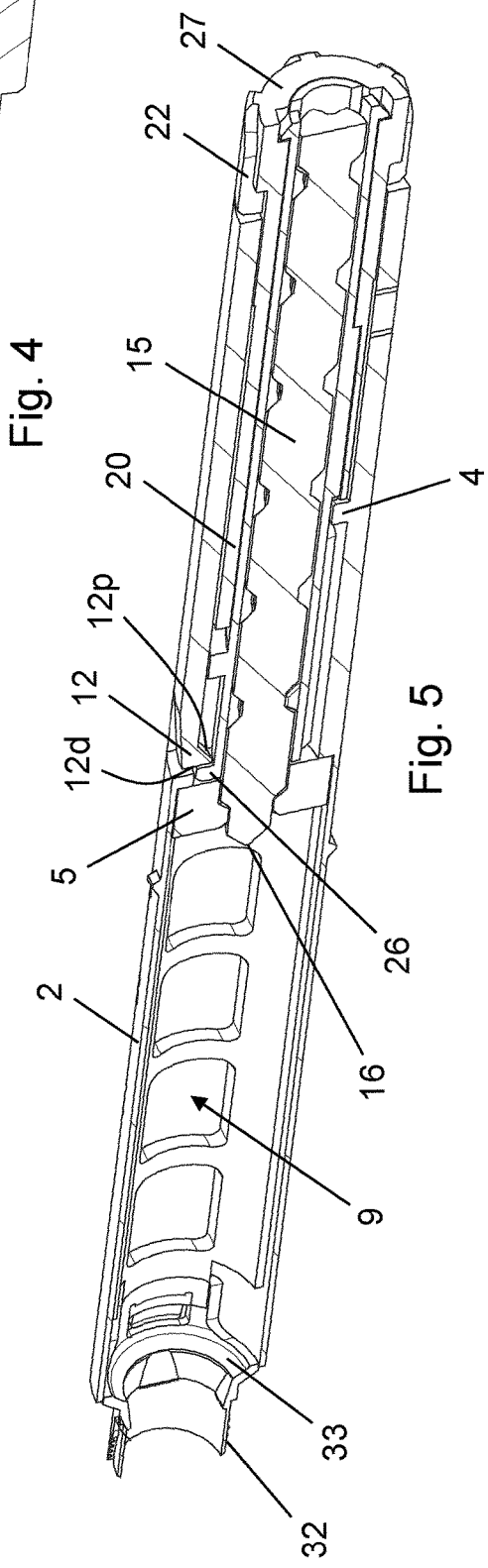

PISTON ROD DRIVE MECHANISM

CROSS-REFERENCE TO RELATED APPLICATIONS

This application is a 35 U.S.C. § 371 National Stage application of International Application PCT/EP2020/084481 (published as WO 2021/110842), filed Dec. 3, 2020, which claims priority to European Patent Application 19213596.0, filed Dec. 4, 2019; the contents of which are incorporated herein by reference.

FIELD OF THE INVENTION

The present invention relates to drug injection devices adapted to deliver the same predetermined dose size at each injection action.

BACKGROUND OF THE INVENTION

Parenteral drug administration carried out using a traditional vial and syringe system is increasingly being substituted by administration using a pen injection device or a prefilled syringe. Such devices are particularly convenient in that they allow the user to perform a dosed injection from a prefilled drug reservoir without first having to manually transfer the particular dose from one reservoir (the vial) to another (the syringe).

Predominantly, two types of pen injection devices are available, durable pen injectors being capable of delivering one or more doses of drug from a prefilled drug cartridge which can be loaded into the device before use and replaced after exhaustion, and disposable pen injectors being capable of delivering one or more doses of drug from a prefilled and nonexchangeable drug cartridge. Each of these types of pen injection devices are, or may in principle be, realised in various sub-types, such as e.g. single-shot devices adapted to deliver only one dose of a predetermined, or selectable, size from a drug cartridge, multi-shot devices capable of delivering a plurality of doses from a drug cartridge, manual devices, where the user provides the force needed for injection, automatic devices having a built-in energy source releasable to occasion the injection, fixed dose devices adapted to deliver a plurality of doses of identical size, variable dose devices offering delivery of a plurality of doses which are each settable by the user from a range of possible dose sizes, etc.

As the labels suggest a durable pen injector is intended for use over a considerable period of time during which multiple drug cartridges are exhausted and replaced, whereas a disposable pen injector is intended for use until its dedicated drug cartridge is exhausted, after which the entire injection device is discarded.

Pen injection devices are conventionally used with matching pen needle assemblies which provide access to a subcutaneous compartment and serve as a means for administration of the drug thereto. Regardless of the type of pen injection device, it is recommended that a pen needle assembly is used only once, to minimise the risk of skin infection and laceration. Prefilled syringes typically come with a staked needle and contain a volume of drug that is administered in one go, after which both syringe and needle are discarded.

While disposable injection devices may be regarded as particularly convenient for the users, requiring fewer handling steps and little or no maintenance, they have a comparably high environmental impact because they are disposed of after only a single or a few dose administrations. In that respect, multi-shot injection devices suffer from the need to be able to deliver a plurality of doses reliably over time and therefore involve relatively complex injection mechanisms with a relatively large number of parts.

WO 2009/092807 (Novo Nordisk A/S) discloses a disposable injection device adapted to deliver a plurality of doses of a fixed dose size. The device has a simple user interface in that a dose is automatically prepared for injection by a cycle of mounting and dismounting of a protective cap and automatically expelled, by means of a spring, at the touch of a button. However, even though the device is simple it contains many different components, made of at least four different types of materials: plastic, metal, rubber and glass. Hence, if such a device is collected for recycling it should be broken down in pieces to separate the individual materials. In view of the large number of disposable injection devices generally present in various treatment segments it would require an automated setup of considerable complexity to properly execute this material separation.

WO 2009/080775 (Novo Nordisk A/S) discloses another disposable injection device adapted to deliver a plurality of doses of a fixed dose size. This device is fully manual in that both dose preparation and dose injection actions require dedicated user operations of a tubular sleeve, comprising rotating the tubular sleeve during dose preparation and depressing the tubular sleeve towards the device housing during dose injection. Accordingly, the device may be realised without any metal parts, but the disclosed piston rod drive mechanism requires a further tubular sleeve, adding to the total number of components in, as well as the complexity of, the construction.

SUMMARY OF THE INVENTION

It is an object of the invention to eliminate or reduce at least one drawback of the prior art, or to provide a useful alternative to prior art solutions.

In particular, it is an object of the invention to provide a disposable multi-shot pen injection device having a comparably low environmental impact.

It is a further object of the invention to provide a simple piston rod drive mechanism for a pen injection device, consisting of only few parts.

It is a further object of the invention to provide such a device and mechanism which is robust and reliable.

In the disclosure of the present invention, aspects and embodiments will be described which will address one or more of the above objects and/or which will address objects apparent from the following text.

In one aspect the invention provides a dose expelling mechanism as defined in claim 1.

Accordingly, a piston rod displacement mechanism, or piston rod drive mechanism, for a pen injection device is provided. The piston rod displacement mechanism comprises a tubular housing extending along a reference axis, a nut member fixed within the tubular housing, a piston rod comprising a first non-self-locking thread having a first thread direction and a first thread pitch and being engaged with the nut member, and a second non-self-locking thread superposed on the first non-self-locking thread, the second non-self-locking thread having a second thread direction and a second thread pitch, and a dose dial sleeve operable to advance the piston rod in the nut member.

The tubular housing comprises an interior housing surface with a first engagement structure, and the dose dial sleeve comprises an exterior sleeve surface with a second engagement structure being in sliding engagement with the first engagement structure, and an interior sleeve surface with a third engagement structure being engaged with the second non-self-locking thread.

One of the first engagement structure and the second engagement structure comprises a closed-circuit track configuration and the other of the first engagement structure and the second engagement structure comprises a track follower. Furthermore, the closed-circuit track configuration comprises a helical track portion having a helical track direction equaling the second thread direction and a helical track pitch equaling the second thread pitch, and an axial track portion extending between a distal track end and a proximal track end and being connected to the helical track portion at the distal track end. The dose dial sleeve is thereby operable to advance the piston rod a predetermined distance in the nut member by helical proximal motion about the piston rod relative to the tubular housing and subsequent translational distal motion along the reference axis relative to the tubular housing.

Hence, by turning the dose dial sleeve relative to the tubular housing the track follower travels the helical track portion until it meets a rotational stop, defining a transition from the helical track portion to the axial track portion at the distal track end. Since the helical track direction equals the second thread direction and the helical track pitch equals the second thread pitch the third engagement structure travels the second non-self-locking thread, and the dose dial sleeve thereby moves helically about the piston rod, when the track follower travels the helical track portion. The piston rod, however, remains stationary relative to the tubular housing due to the engagement between the first non-self-locking thread and the nut member. Resultantly, the dose dial sleeve undergoes a proximal helical displacement relative to the tubular housing, in preparation of the eventual displacement of the piston rod.

By subsequently pressing the dose dial sleeve distally relative to the tubular housing the track follower travels the axial track portion until it meets an axial stop, defining a transition from the axial track portion to the helical track portion, or to a second helical track portion, at the proximal track end. Due to the piston rod comprising oppositely directed superposed threads, in the form of the first non-self-locking thread and the second non-self-locking thread, the translational movement of the dose dial sleeve results in a distal helical displacement of the piston rod relative to the tubular housing. The extent of this distal helical displacement of the piston rod, i.e. the advancement of the piston rod, is determined by the ratio of the first thread pitch to the second thread pitch, as the translational movement of the dose dial sleeve also results in a relative axial motion between the piston rod and the dose dial sleeve.

Since the ratio of the first thread pitch to the second thread pitch is chosen by the manufacturer the piston rod displacement mechanism is constructed to provide a predetermined axial displacement of the piston rod relative to the tubular housing at each cycle of the track follower travelling the helical track portion and the axial track portion. A very simple and reliable piston rod displacement mechanism for a pen injection device is thereby provided, made from only three components, the tubular housing, the dose dial sleeve, and the piston rod. In view of the few parts and the fact that they may all be formed using the same material, e.g. recyclable plastic, the solution presents an environmentally attractive alternative to prior art disposable injection device mechanisms.

In exemplary embodiments of the invention the helical track portion and the axial track portion are further connected at the proximal track end, and the closed-circuit track configuration thereby comprises a single helical track portion and a single axial track portion. In order to perform the predetermined axial displacement of the piston rod the dose dial sleeve is thus firstly turned 360°, until the track follower meets the rotational stop at the distal track end, and secondly pressed towards the housing until the track follower meets the axial stop at the proximal track end.

In other embodiments of the invention, the closed-circuit track configuration comprises a second helical track portion connected to the axial track portion at the proximal track end, and a second axial track portion extending between a second distal track end and a second proximal track end being connected to the second helical track portion at the second distal track end and to the helical track portion at the second proximal track end. The predetermined axial displacement of the piston rod is thereby performed twice for one full revolution of the dose dial sleeve.

One of the interior housing surface and the exterior sleeve surface may comprise a corrugated portion, i.e. a number of alternating axially extending ridges and grooves, and the other of the interior housing surface and the exterior sleeve surface may comprise a flexibly supported radial protrusion configured to ride over the corrugated portion during helical motion of the dose dial sleeve relative to the tubular housing. Thereby, when the dose dial sleeve is rotated about the reference axis relative to the tubular housing the radial protrusion will successively snap over the axially extending ridges and produce an audible and tactile feedback to the user, in the form of click sounds and jolting, which signals that the piston rod displacement mechanism is being prepared to advance the piston rod.

The corrugated portion may comprise a state shifting ridge, and the radial protrusion may be configured to pass the state shifting ridge and enter an axially extending dose groove in response to the track follower reaching the distal track end during helical proximal motion of the dose dial sleeve relative to the tubular housing. The state shifting ridge may be configured to prevent reverse motion of the radial protrusion, thereby preventing return motion of the track follower along the helical track portion.

Until the track follower reaches the distal track end it is thus possible for the user to regret an initiated preparation action, as a reverse rotation of the dose dial will cause the radial protrusion to ride over the corrugated portion in the opposite direction, while the track follower travels back in the helical track portion. However, once the radial protrusion passes the state shifting ridge the user can no longer regret the preparation action and the piston rod displacement mechanism is irreversibly readied to displace the piston rod by depression of the dose dial.

The state shifting ridge may be steeper than the other ridges and the dose groove may be deeper than the other grooves of the corrugated portion. Thereby, when the radial protrusion passes the state shifting ridge a distinctly louder click sound is emitted, indicating that the preparation action is completed.

The dose groove may comprise a plurality of axially spaced apart elevations which the radial protrusion passes during translational distal motion of the dose dial sleeve relative to the tubular housing. This will provide an audible and tactile feedback to the user, signalling that the piston rod displacement is ongoing. The elevations may be configured to provide for unidirectional passage of the radial protrusion to thereby prevent the user from suddenly reversing the direction of motion of the dose dial sleeve in the tubular housing during a piston rod displacement action.

The dose groove may comprise a distal end configured to engage the radial protrusion and thereby limit proximal displacement of the dose dial sleeve relative to the tubular housing. This will prevent accidental separation of the dose dial sleeve from the tubular housing when the track follower is positioned at the distal track end, being prepared to travel the axial track portion.

One of the interior housing surface and the exterior sleeve surface may comprise a flexible snap arm, and the other of the interior housing surface and the exterior sleeve surface may comprise a snap geometry, and the flexible snap arm may be configured to snap over the snap geometry in response to the track follower reaching the proximal track end during translational distal motion of the dose dial sleeve relative to the tubular housing. Thereby, a distinct click sound may be emitted, providing a feedback to the user that the piston rod displacement action is completed.

The flexible snap arm and the snap geometry may be configured to prevent proximal translational motion of the dose dial sleeve relative to the tubular housing when the track follower is at the proximal track end. This will prevent return motion of the track follower along the axial track portion after completed piston rod displacement and ensure that the only way to continue operating the piston rod displacement mechanism is by turning the dose dial sleeve about the reference axis to lead the track follower distally in the helical track portion in preparation of a next piston rod displacement action.

The tubular housing may comprise a plurality of axially distributed windows, allowing visual inspection of an interior housing portion. The plurality of axially distributed windows may be pair-wise axially offset a distance corresponding to the predetermined axial displacement exhibited by the piston rod relative to the tubular housing as the track follower travels the axial track portion from the distal track end to the proximal track end during translational distal motion of the dose dial sleeve relative to the tubular housing. It is then possible to arrange the plurality of axially distributed windows such that a distal end portion of the piston rod shifts distally from one window to a neighbouring window during a piston rod displacement action. This will allow the user to keep track of the number of times the piston rod displacement mechanism has been activated and the number of times the piston rod displacement mechanism may still be activated.

In another aspect the invention provides a pen injection device comprising a piston rod displacement mechanism as described above.

The pen injection device may comprise a drug cartridge holding a volume of drug substance in a cartridge body between a penetrable self-sealing septum and a slidable piston, and the piston rod may abut the slidable piston, or an intermediate component connected to the slidable piston, such as e.g. a piston washer. The pen injection device may further comprise, or be adapted to receive, a pen needle assembly comprising an injection needle with a front portion for insertion into the skin of the user and a rear portion for insertion into the drug cartridge through the penetrable self-sealing septum.

In the pen injection device with a received pen needle assembly an axial displacement of the piston rod results in an equal axial displacement of the slidable piston, which causes an expelling of a correlated volume of the drug substance through the injection needle. The pen injection device is thus configured to deliver multiple doses of a predetermined dose size.

The volume of drug substance, along with the closed-circuit track configuration, the first thread pitch, and the second thread pitch, are then decisive of the number of doses of the predetermined dose size which the pen injection device offers. In exemplary embodiments of the invention the tubular housing comprises a plurality of axially distributed windows which are pairwise axially offset a distance corresponding to the predetermined axial displacement exhibited by the piston rod during translational distal motion of the dose dial sleeve. The number of axially distributed windows equals the number of doses of the predetermined dose size initially expellable by the pen injection device and are arranged such that a distal end portion of the piston rod shifts distally from one window to a neighbouring window during a piston rod displacement action. This allows the user to keep track of the number of remaining expellable doses in an easy manner, by counting the number of windows where the piston rod is not yet visible.

For the avoidance of any doubt, in the present context the term "injection device" designates an apparatus suitable for injecting fluid media into the body of a subject, e.g. with the aid of an attachable needle device, and the term "drug" designates a medium which is used in the treatment, prevention or diagnosis of a condition, i.e. including a medium having a therapeutic or metabolic effect in the body. Further, the terms "distal" and "proximal" denote positions at, or directions along, a drug delivery device, a drug reservoir, or a needle unit, where "distal" refers to the drug outlet end and "proximal" refers to the end opposite the drug outlet end.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein FIG. 2 is a longitudinal section perspective view of a housing of the injection device, FIG. 3 is a perspective view of a combined dose preparation and injection button of the injection device, FIG. 4 is a longitudinal section perspective view of the combined dose preparation and injection button, and FIG. 5 is a longitudinal section perspective view of the injection device in an assembled state (still without the drug container).

In the figures like structures are mainly identified by like reference numerals.

DESCRIPTION OF EXEMPLARY EMBODIMENTS

Figure 1:
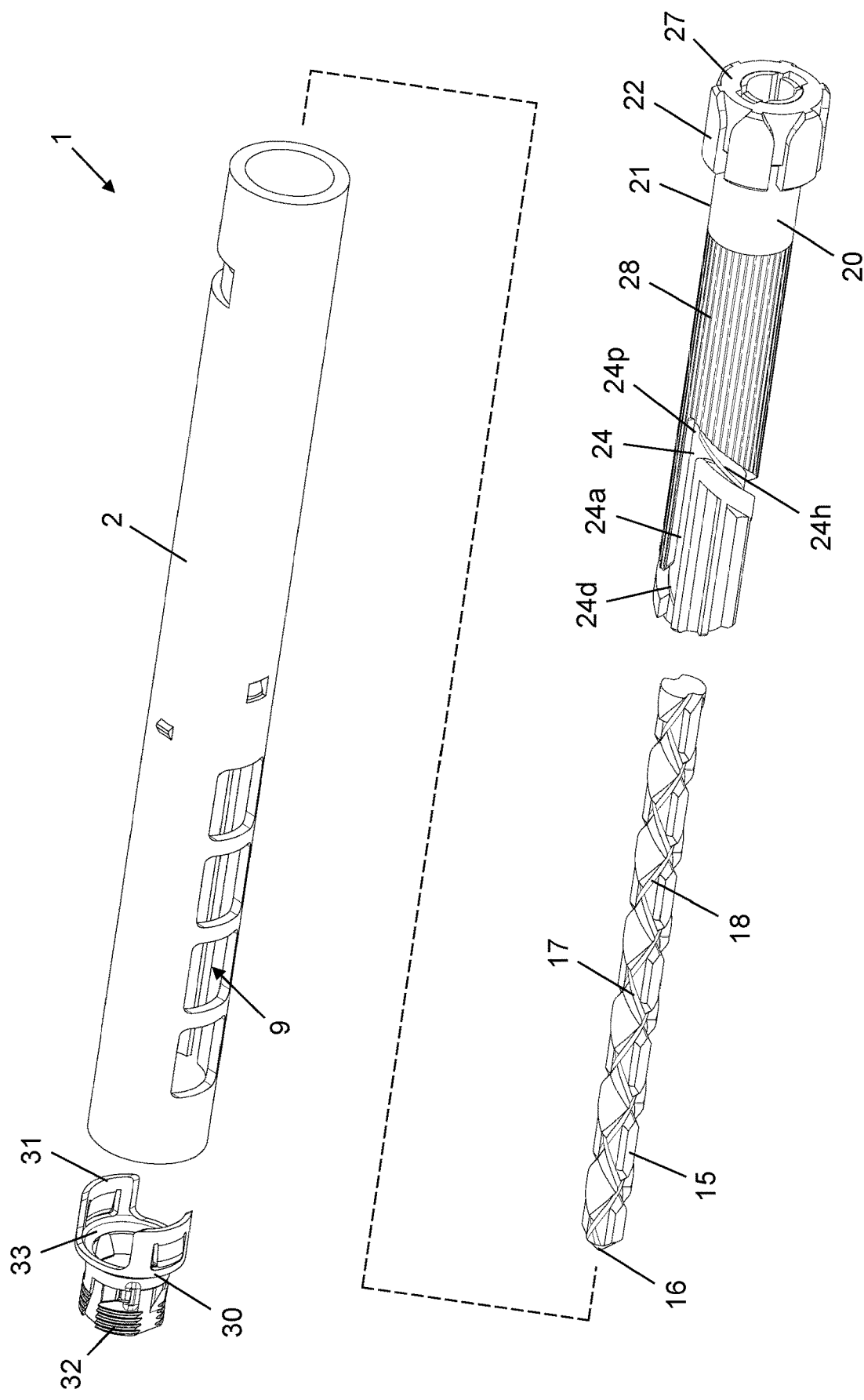
FIG. 1 is an exploded view of an injection device according to exemplary embodiment of the invention, albeit without a drug container.

When/If relative expressions, such as "upper" and "lower", "left" and "right", "horizontal" and "vertical", "clockwise" and "counter-clockwise", etc., are used in the following, these refer to the appended figures and not necessarily to an actual situation of use. The shown figures are schematic representations for which reason the configuration of the different structures as well as their relative dimensions are intended to serve illustrative purposes only.

FIG. 1 is an exploded view of an injection device 1 according to an exemplary embodiment of the invention. It is noted that the figure does neither show the drug container carrying the drug to be administered by the injection device 1, nor the injection needle assembly that is adapted for use with the injection device 1 to deliver the drug to a desired injection site. The drug container and the injection needle assembly could in principle each be one of a plurality of different possible types. However, for the present embodiment it is particularly envisaged that they each be types conventionally used with pen injection devices, i.e. a cartridge type container having a generally cylindrical container body with a necked down outlet end portion being sealed by a penetrable self-sealing septum and an axially opposite portion being sealed by a slidable piston, respectively a needle unit with a needle hub, in which an injection needle is fixedly mounted, and a skirt portion comprising means for releasable attachment to the injection device 1.

The injection device 1 comprises a housing 2 which extends along a longitudinal axis and a cartridge holder 30 in axial extension thereof. The cartridge holder 30 has a pair of opposite flanges 31 adapted to snap fit to the housing 2 and a needle mount 32 for reception of the injection needle assembly described above. A shoulder portion 33 connects the flanges 31 and the needle mount 32 and serves to retain the drug container described above. Four windows 9 are arranged axially in line in a distal half of the housing 2 to allow inspection of the contents of the drug container.

The housing 2 forms part of a dose expelling mechanism of the injection device 1, together with a piston rod 15 and a dose dial 20. The piston rod 15 is double-threaded in that it has two oppositely handed non-self-locking threads superposed on one another, a dial connecting thread 17 and a nut connecting thread 18. The piston rod 15 is adapted to advance helically relative to the housing 2 during dose expelling, in a manner that will be described in further detail below, to thereby advance the slidable piston in the generally cylindrical container body. For that, a leading end 16 of the piston rod 15 is configured to abut the slidable piston, or a piston washer connected to the slidable piston.

The dose dial 20 has a tubular dial body 21 with a proximal dial head 22 for easy user operation. The dial head 22 has an end face 27 prepared for reception of e.g. a thumb of the user. A portion of the exterior surface of the dial body 21 is provided with axial corrugations 28 which are interrupted distally by a track configuration 24. The track configuration 24 extends circumferentially about the dial body 21 and comprises a helical dose preparing track segment 24*h* and an axial dosing track segment 24*a*. The two track segments are connected distally at a distal junction 24*d* and proximally at a proximal junction 24*p*. Notably, the direction and the pitch of the helical dose preparing track segment 24*h* corresponds to the direction and the pitch of the dial connecting thread 17.

FIG. 2 is a longitudinal section perspective view showing an interior of the housing 2. A nut member 5 having a nut thread 8 is fixed in the housing 2 and divides the interior thereof in a proximal space 6 and a distal space 7. The proximal space 6 is configured to accommodate the piston rod 15 and the dose dial 20 and is delimited by an interior housing surface 3, from which a knob 4 protrudes radially. A proximal housing snap 11 is provided on a flexible arm formed by a removal of surrounding housing material. The proximal housing snap 11 has a proximally facing inclined cut 11*p*. The distal space 7 is configured to accommodate the drug container which is held in place by the cartridge holder 30 whose flanges 31 extend into a distal opening 10 of, and are laser welded to, the housing 2.

FIG. 3 is a perspective view of the dose dial 20, from a different angle than the one of FIG. 1. In particular, FIG. 3 shows an axial groove 25 formed in the axial corrugations 28 and a distal step 26 formed at a distal end of the dial body 21. The axial groove 25, which terminates distally at a distal groove end 25*d*, is provided with five transversal ribs 25*t*, axially equidistantly spaced apart from each other. FIG. 4 is a longitudinal section perspective view of the dose dial 20, showing an interior dial surface 23, on a distal portion of which is formed a thread segment 29.

FIG. 5 is a longitudinal section perspective view of the housing 2, the piston rod 15, the dose dial 20, and the cartridge holder 30 as assembled. It reveals that the housing 2 also has a distal housing snap 12, which in the depicted state of the injection device 1 is positioned just proximally of the distal step 26. The distal housing snap 12 is formed with a proximal inclined surface 12*p* and a distal steep surface 12*d*, respectively allowing the distal housing snap 12 to be lifted and passed by the distal step 26 during distal translational motion of the dose dial 20 relative to the housing 2, and preventing subsequent proximal translational motion of the dose dial 20 relative to the housing 2 by preventing return passage of the distal step 26.

When assembled, the knob 4 is slidably occupied in the track configuration 24, the nut connecting thread 18 is engaged with the nut thread 8, and the dial connecting thread 17 is engaged with the thread segment 29. This provides a very simple and inexpensive piston rod displacement mechanism based on only three components. As such, the whole of the injection device 1, perhaps apart from the drug container, may be manufactured using only recyclable plastic, and given the few components needed to expel doses of drug from the drug container, the injection device 1 can be realised with a relatively low environmental impact.

In the following the mode of operation of the injection device 1 will be demonstrated with reference to the figures.

The track configuration 24 forms a circumferentially closed loop or circuit on the exterior surface of the dial body 21. This closed loop consists of the mentioned helical dose preparing track segment 24*h* and the axial dosing track segment 24*a*. In the assembled state of the injection device 1 shown in FIG. 5 the dial body 21 is fully occupied in the proximal space 6 and only the dial head 22 extends proximally beyond the housing 2. This corresponds to a non-prepared state of the injection device 1 in which no dose is ready to be expelled from the (not shown) drug container. In this state the knob 4 is positioned at the proximal junction 24p, which constitutes the beginning of the helical dose preparing track segment 24h as well as the end of the axial dosing track segment 24a.

In order to expel a dose of drug from the injection device 1 the user firstly grabs the housing 2 and turns the dial head 22 clockwise (seen from a proximal perspective) relative thereto. The clockwise rotation of the dial head 22 causes a clockwise rotation of the dial body 21, whereby the knob 4 begins to travel the helical dose preparing track segment 24h and the thread segment 29 begins to travel the dial connecting thread 17. The piston rod 15 remains stationary due to the engagement with the nut member 5. As the dose dial 20 is thereby both angularly and axially displaced relative to the housing 2 the proximal housing snap 11 rides over the axial corrugations 28, producing a clicking sound at each passage of a ridge, which is an audible feedback to the user that a dose is being prepared.

So long as the knob 4 has not yet reached the distal junction 24d, which constitutes the end of the helical dose preparing track segment 24h and the beginning of the axial dosing track segment 24a, the user may regret her initiated action and turn the dial head 22 counter-clockwise, which will take the knob 4 back to the proximal junction 24p, while the proximal housing snap 11 rides reversely over the axial corrugations 28. The dose dial 20 thus returns to the position shown in FIG. 5.

However, once the dose dial 20 is rotated 360° about the longitudinal axis and the knob 4 reaches the distal junction 24d the proximal housing snap 11 passes a non-return ridge of the axial corrugations 28 and enters the axial groove 25. At this point the user can no longer reverse the direction of rotation of the dial head 22 and a dose has been prepared for delivery. The non-return ridge and the axial groove 25 are configured such that on passage of the proximal housing snap 11 a distinctly louder click sound is emitted, signalling to the user that the dose preparing action is completed.

After passing the non-return ridge the proximal housing snap 11 is positioned at the distal groove end 25d. The distal groove end 25d is configured to engage the proximal housing snap 11 and thereby prevent proximal translational motion of the dose dial 20 relative to the housing 2. This ensures that the user cannot by accident pull out the dose dial 20 from the housing 2.

With the knob 4 now positioned at the distal junction 24d the injection device 1 is ready to expel a dose of drug from the drug container. After having inserted an injection needle of an attached needle unit (not shown) through the skin at a desired injection site the user simply pushes the dose dial 20 towards the housing 2 by applying an axial force to the end face 27. The knob 4 will thereby begin to travel the axial dosing track segment 24a and the resulting translational displacement of the dial body 21 will cause the piston rod 15 to rotate in the nut member 5, due to the engagement between the thread segment 29 and the dial connecting thread 17. The engagement between the nut thread 8 and the nut connecting thread 18 resultantly leads to a helical distal displacement of the piston rod 15 which thereby advances through the nut member 5.

When the knob 4 reaches the proximal junction 24p the piston rod has been displaced a certain axial distance which depends on the pitch ratio of the dial connecting thread 17 to the nut connecting thread 18. In the present case the pitch of the former equals that of the latter, so the axial displacement of the piston rod 15 is half the axial displacement of the dose dial 20. Since the axial displacement of the piston rod 15 decides the axial displacement of the slidable piston in the drug container the length of the axial dosing track segment 24a effectively determines the size of the expelled dose. The injection device 1 is thus designed to expel the same predetermined amount of drug at each dose expelling action.

Due to the non-self-locking thread interfaces between the dial connecting thread 17 and the thread segment 29, respectively the nut connecting thread 18 and the nut thread 8 a very low axial force is required to advance the piston rod 15 through the nut member 5, which is attractive from a user perspective. Furthermore, since the piston rod 15 can only be advanced when the knob 4 travels the axial dosing track segment 24a it is not possible to purposely or accidentally inject a larger dose than the one which the injection device is designed to deliver. The closed-circuit track configuration 24 provides for a very simple user interface, where each dose can be administered by merely turning the dial head 22 as far as possible (360°) and subsequently depress the dial head 22 towards the housing 2 until it meets a stop. The dose dial 20 returns to its initial position in the housing 2 after each dose expelling action.

During the translational motion of the dose dial 20 into the housing 2 in connection with a dose expression, as the knob 4 travels the axial dosing track segment 24a from the distal junction 24d to the proximal junction 24p, the proximal housing snap 11 successively passes the transversal ribs 25t by virtue of the proximally facing inclined cut 11p, thereby producing click sounds that serve to audibly and tactilely verify that an injection is ongoing. As the knob 4 reaches the proximal junction 24p the inclined surface 12p slides over the distal step 26, whereby elastic energy is transiently stored in the distal housing snap 12, deflecting radially away from a rest position. As the steep surface 12d passes the distal step 26 the elastic energy is released and the distal housing snap 12 returns to the rest position, emitting a distinctly louder click sound which signals to the user that the dose expelling action is completed.

The steep surface 12d now interfaces the distal step 26 and prevents proximal translational motion of the dose dial 20 relative to the housing 2. This ensures that the user cannot force the knob 4 to travel the axial dosing track segment 24a in the opposite direction. Hence, the only way to continue using the injection device 1 is by once again turning the dial head 22 clockwise relative to the housing 2 which will lead the knob 4 from the proximal junction 24p into the helical dose preparing track segment 24h in preparation for the next dose administration.

The injection device 1 of the present embodiment is configured to deliver four predetermined doses of a particular dose size from the drug container. The four windows 9 are arranged accordingly such that the slidable piston is visible in the proximal most window after delivery of the first dose, in the neighbouring window after delivery of the second dose, and so forth. The user can thereby easily see how many doses remain to be administered with the injection device 1.

The invention claimed is:
1. A piston rod displacement mechanism for a pen injection device, comprising:
   a tubular housing extending along a reference axis and comprising an interior housing surface with a first engagement structure,
   a nut member fixed within the tubular housing,
   a piston rod comprising a first non-self-locking thread having a first thread direction and a first thread pitch and being engaged with the nut member, and a second non-self-locking thread superposed on the first non- self-locking thread, the second non-self-locking thread having a second thread direction and a second thread pitch, and a dose dial sleeve operable to advance the piston rod in the nut member, the dose dial sleeve comprising an exterior sleeve surface with a second engagement structure being in sliding engagement with the first engagement structure, and an interior sleeve surface with a third engagement structure being engaged with the second non-self-locking thread, wherein one of the first engagement structure and the second engagement structure comprises a closed-circuit track configuration and the other of the first engagement structure and the second engagement structure comprises a track follower, and wherein the closed-circuit track configuration comprises a helical track portion having a helical track direction equalling the second thread direction and a helical track pitch equalling the second thread pitch, and an axial track portion extending between a distal track end and a proximal track end and being connected to the helical track portion at the distal track end, the dose dial sleeve thereby being operable to advance the piston rod a predetermined distance in the nut member by helical proximal motion about the piston rod relative to the tubular housing and subsequent translational distal motion along the reference axis relative to the tubular housing.

2. The piston rod displacement mechanism according to claim 1, wherein one of the interior housing surface and the exterior sleeve surface comprises a corrugated portion and the other of the interior housing surface and the exterior sleeve surface comprises a flexibly supported radial protrusion configured to ride over the corrugated portion during helical motion of the dose dial sleeve relative to the tubular housing.

3. The piston rod displacement mechanism according to claim 2, wherein the corrugated portion comprises a state shifting ridge, and wherein the flexibly supported radial protrusion is configured to pass the state shifting ridge and enter an axially extending dose groove in response to the track follower reaching the distal track end during helical proximal motion of the dose dial sleeve relative to the tubular housing, the state shifting ridge being configured to prevent reverse motion of the flexibly supported radial protrusion, thereby preventing return motion of the track follower along the helical track portion.

4. The piston rod displacement mechanism according to claim 3, wherein the axially extending dose groove comprises a plurality of axially spaced apart elevations which the flexibly supported radial protrusion passes during translational distal motion of the dose dial sleeve relative to the tubular housing.

5. The piston rod displacement mechanism according to claim 3, wherein the axially extending dose groove has a distal groove end configured to engage the flexibly supported radial protrusion and thereby limit proximal displacement of the dose dial sleeve relative to the tubular housing.

6. The piston rod displacement mechanism according to claim 1 wherein one of the interior housing surface and the exterior sleeve surface comprises a flexible snap arm and the other of the interior housing surface and the exterior sleeve surface comprises a snap geometry, and wherein the flexible snap arm is configured to snap over the snap geometry in response to the track follower reaching the proximal track end during translational distal motion of the dose dial sleeve relative to the tubular housing.

7. The piston rod displacement mechanism according to claim 6, wherein the flexible snap arm and the snap geometry are configured to prevent proximal translational motion of the dose dial sleeve relative to the tubular housing when the track follower is at the proximal track end.

8. The piston rod displacement mechanism according to claim 1, wherein the tubular housing comprises a plurality of axially distributed windows, the plurality of axially distributed windows being pair-wise axially offset a distance corresponding to an axial distance which the piston rod advances as the track follower travels the axial track portion from the distal track end to the proximal track end during translational distal motion of the dose dial sleeve relative to the tubular housing.

9. The piston rod displacement mechanism according to claim 1, wherein the axial track portion is further connected to the helical track portion at the proximal track end, the closed circuit track configuration thereby comprising a single helical track portion and a single axial track portion.

10. A pen injection device comprising a piston rod displacement mechanism according to claim 1.

* * * * *